(12) United States Patent
Johns et al.

(10) Patent No.: US 7,815,311 B2
(45) Date of Patent: Oct. 19, 2010

(54) ALERTNESS SENSING SPECTACLES

(75) Inventors: Murray Johns, Richmond (AU); Aaron Brown, Richmond (AU)

(73) Assignee: Sleep Diagnostics Pty., Ltd, Richmond, Victoria (AU)

( * ) Notice: Subject to any disclaimer, the term of this patent is extended or adjusted under 35 U.S.C. 154(b) by 351 days.

(21) Appl. No.: 12/063,130

(22) PCT Filed: Aug. 10, 2006

(86) PCT No.: PCT/AU2006/001131
§ 371 (c)(1),
(2), (4) Date: Feb. 7, 2008

(87) PCT Pub. No.: WO2007/016739
PCT Pub. Date: Feb. 15, 2007

(65) Prior Publication Data
US 2010/0134761 A1    Jun. 3, 2010

(30) Foreign Application Priority Data
Aug. 11, 2005    (AU) ............................. 2005904308

(51) Int. Cl.
*A61B 3/14*    (2006.01)
*A61B 3/00*    (2006.01)
(52) U.S. Cl. .................. 351/209; 351/210; 351/246

(58) Field of Classification Search .......... 351/200–246
See application file for complete search history.

(56) References Cited

U.S. PATENT DOCUMENTS

| 4,145,122 A * | 3/1979 | Rinard et al. ............... 351/210 |
| 4,659,197 A * | 4/1987 | Weinblatt .................... 351/210 |
| 4,852,988 A * | 8/1989 | Velez et al. .................. 351/210 |
| 5,745,038 A * | 4/1998 | Vance .......................... 340/575 |

FOREIGN PATENT DOCUMENTS

| DE | 10015200 | 10/2001 |
| JP | 11151298 | 6/1999 |

* cited by examiner

*Primary Examiner*—Mohammed Hasan
(74) *Attorney, Agent, or Firm*—Connolly Bove Lodge & Hutz LLP; Morris Liss (57) ABSTRACT

Spectacles for use in an eye monitoring system include a pair of ocular frames and a sensor unit adapted to be positioned adjacent an eye of the wearer. A nose bridge connects the ocular frames and incorporates an adjustment mechanism for adjusting the vertical position of the sensor unit relative to the eye. A frame arm extends from the outer edge of each ocular frame and is adapted to fit over the ear of a wearer. The sensor unit incorporates two infra red emitters at different angles and an infra red detector recessed into the surface of the unit to reduce the proportion of signal received by said detector which is not from the signal emitter reflected by the eye or eyelids.

11 Claims, 8 Drawing Sheets

Sensor position relative to eye

Sensor position relative to frame (top view of frame)

ALERTNESS SENSING SPECTACLES

CROSS REFERENCE TO RELATED APPLICATIONS

This application is a National Phase filing under 35 U.S.C. §371 of PCT/AU2006/001131 filed Aug. 10, 2006, which claims priority to Patent Application No. 2005904308, filed in Australia on Aug. 11, 2005. The entire contents of each of the above-applications are incorporated herein by reference.

This invention relates to spectacles used in monitoring eye and eyelid movement.

BACKGROUND TO THE INVENTION

The detection of drowsiness is of importance because drowsiness impairs the ability of operators of a wide range of equipment including motor vehicles, aircraft and boats as well as industrial equipment. The problem of drowsy driving cannot be solved by educating drivers to take remedial action when feeling drowsy. The difficulty is that many people are unaware of their drowsiness before and during the drowsiness even though they may be alert and aware after they rouse. This means one cannot predict when their level of drowsiness will next decrease to the point of danger because the drowsy state involves a loss of awareness of the present; an involuntary lapse of attention.

U.S. Pat. No. 5,745,038 discloses an eye monitor that examines reflected light from the eye to detect blinking behavior as an indicator of drowsiness.

U.S. Pat. No. 6,097,295 discloses a system of image analysis based on eye pupil size.

U.S. Pat. No. 6,147,612 discloses a system of preventing sleep which detects eyelid movement and actuates an alarm when the eyelid movement is indicative of drowsiness.

U.S. Pat. No. 6,346,887 uses a video based eye tracking system which tracks eye activity and pupil diameter and position to produce a signal representing eye activity that can be used to estimate alertness.

WO 03/039358 disclosed an alertness monitor that used infra red light to measure the amplitude and velocity of eyelid and eye movements to derive a measure of alertness on a scale that can be related to the scale of blood alcohol levels. This monitor sought to provide a real time alertness monitor that can provide a calibrated measure of the operator's alertness. The quality of the signals received from the light reflected off the eye and eyelid depends in part on the orientation of the emitters and detectors.

Adjustable frames for spectacles are known but generally are adjustable to accommodate the distance between the pupils and the distance between the mid point of the eyes and the bridge of the nose.

U.S. Pat. No. 5,583,586 provides a support system for spectacles which spaces the frame from the cheek bones and brow of the wearer.

Testing apparatus for examining eyes usually include fittings adjustable in several directions.

U.S. Pat. No. 4,448,501 discloses trial spectacles with means to vary the lens positions.

U.S. Pat. No. 5,499,063 discloses an adjustable nose bridge and means to move the lenses.

EP 567817 discloses trial frames which allow adjustment in the plane parallel to the face and also away from the face.

U.S. Pat. No. 4,730,898 provides a stereoscopic viewer with frames that allow the device to be adjustable in length relative to the ears.

U.S. Pat. No. 5,971,538 discloses a head mounted virtual reality display with an articulated nose bridge that allows the position of the display relative to the eyes to be adjustable.

It is an object of this invention to provide spectacles for an eye monitoring system of the type disclosed in WO 03/039358.

BRIEF DESCRIPTION OF THE INVENTION

To this end the present invention provides a spectacle frame for use in an eye monitoring system which includes
a) a nose bridge connecting a pair of ocular frames
b) a sensor unit adjustably attached to said nose bridge said sensor unit incorporating a signal emitter and a signal detector recessed into the surface of the unit to reduce the proportion of signal received by said detector which is not from the signal emitter reflected by the eye or eyelids
c) said nose bridge incorporating an adjustment mechanism for adjusting the vertical position of said sensor unit relative to the eye
d) a frame arm extending from the outer edge of each ocular frame adapted to fit over the ear of a wearer wherein one of said frame arms incorporates a microprocessor for controlling the sensor unit.

This invention is partly predicated on the discovery that the collection of reflected signals from the eye and eyelids depends on the vertical and horizontal spacing of the emitter and detector from the eye as well as the arrangement of the emitter and detector relative to one another.

The spectacles are preferably designed to be worn by vehicle drivers or machinery operators to measure their level of alertness or fatigue. The spectacles contain one or more clusters of transducers called the sensor unit. The sensor unit is designed into the spectacles and positioned so the sensor signal is reflected from the driver's eyes. The signal emitters may be LED's or the terminal ends of optical fibres connected to a light source such as an LED. The preferred signal is light in the infra red wavelength region but any signal reflected from the eyelid or eye such as ultrasound or another electromagnetic frequency band may be used.

Due to the significant differences in human facial structure, the metrics need to be maintained from person to person through a process of fitment which allows the spectacles to be adjusted to a static position on each individual. This allows collection of quality eye movement data (EMD) on a fixed, stable platform whilst being comfortable and unobtrusive to the vision of the user.

The noses bridge needs to be adjustable both vertically and horizontally from the eye and this is achieved by adjusting the position of the bridge along the nose and then adjusting the height relative to the nose. This may be achieved by using a support for the bridge which is sized to suit the varying nose and eye positions in the various facial types. In addition fine adjustments can be made to the sensor arm to adjust the sensor position relative to the nose bridge.

The ocular frames secured to the nose bridge may contain prescribed optical lenses or sun protection lenses which can be elevated out of the line of sight without having to remove the spectacle frames so that the sensor position is not disturbed while the spectacle frame is in use.

In another embodiment this invention provides a spectacle frame for use in an eye monitoring system which includes
a) a pair of ocular frames at least one of which carries a sensor unit adapted to be positioned adjacent an eye of the wearer b) a nose bridge connecting said ocular frames and incorporating an adjustment mechanism for adjusting the vertical position of said sensor unit relative to the eye
c) a frame arm extending from the outer edge of each ocular frame adapted to fit over the ear of a wearer said frame arm being pivotally connected to said ocular member by a hinge that is adjustable
d) said sensor unit incorporating a light (preferably infra red) emitter and a light (preferably infra red) detector recessed into the surface of the unit to reduce the proportion of signal received by said detector which is not from the signal emitter reflected by the eye or eyelids.

The electronics unit which controls the emitters and collects the data from the sensor may be located in the arm of the spectacle frame. This may be connected by cable or wirelessly to a more complex processor and data recording and display unit. Alternatively the processing may be carried out in a processor located on the frame and the display may be an audible signal or voice indicating the wearers fatigue state. This display unit may be a black box type recording unit but may also display the wearer's state of alertness as described in WO 03/039358.

The frames of this invention are modified conventional spectacle frames and can incorporate optical lenses to compensate for visual impairment and may incorporate solar lenses for use in situations where conventional sunglasses are useful. They may also be used without any lenses.

DETAILED DESCRIPTION OF THE INVENTION

A preferred embodiment of the invention will now be described with reference to the drawings in which:

FIG. 16 illustrates location of the embodiment of FIG. 7 relative to the nose and eyes of a wearer;

FIGS. 17A B and C illustrate 3 views of the frame of this invention incorporating a nose adjustment piece;

The spectacles are part of a system of the type disclosed in patent specification WO 03/039358 the contents of which are incorporated herein by reference.

Figure 1:
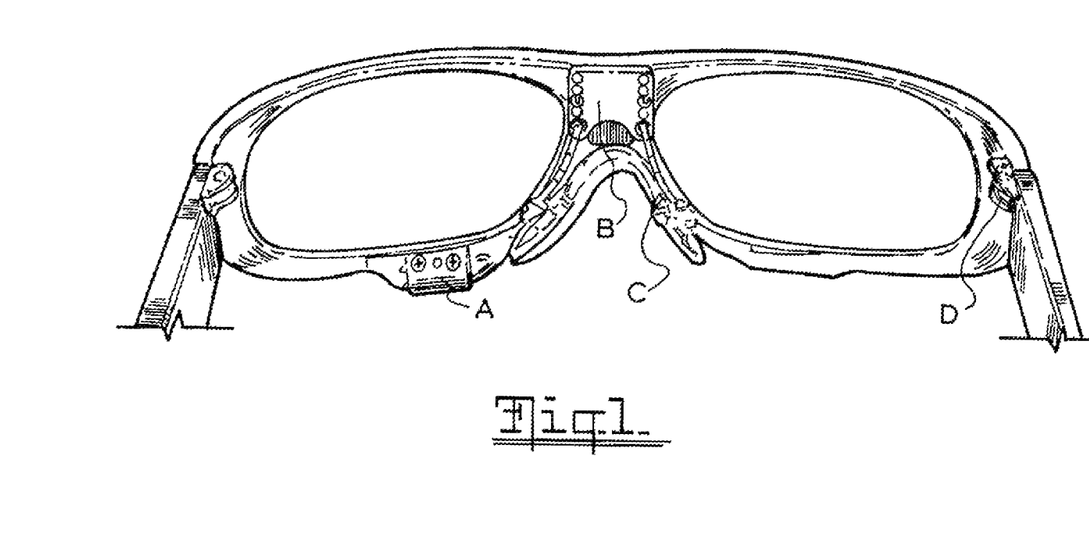
FIG. 1 is a rear view of the spectacles according to a first embodiment of the invention.

In FIG. 1 the sensor assembly A is located on the lower portion of one ocular frame member.

The nose piece B connects the two ocular frame members and by way of the adjustable nose piece arm C allows the vertical location of the ocular frames. The adjustable frame arm hinge D allows movement of the ocular frames relative to the frame arm.

Figure 2:
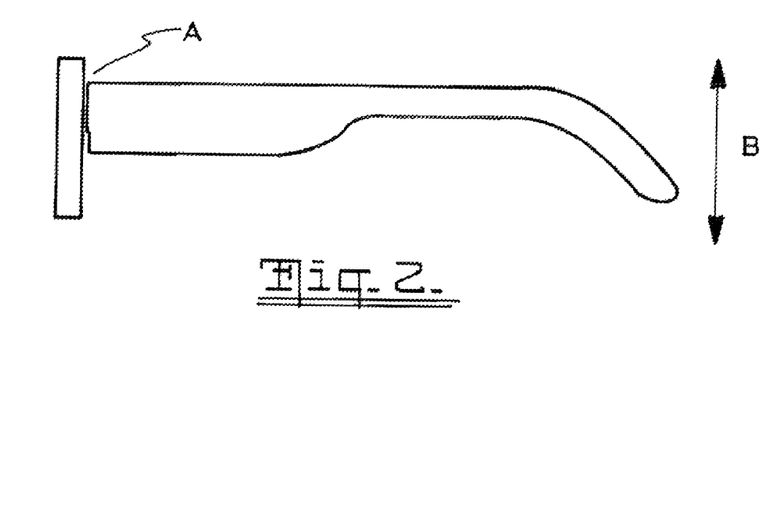
FIG. 2 is a schematic view of the connection between the ocular frame and the frame arm.
Figure 3:
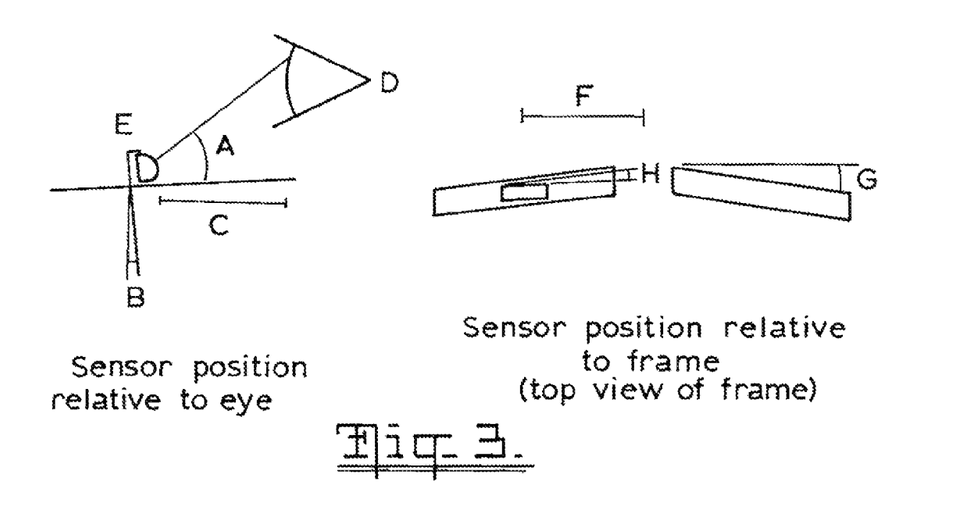
FIG. 3 illustrates the relationship between the position of sensor unit and the eye.

FIG. 2 is a side view of frame arm showing hinge point A where arms can be bent and at B where frame arm can be bent up or down if required This invention is based on research which shows that the key metrics vital for good quality of signal (QOS) from the largest portion of the population depends on the sensor angle relative to user's eye (Left) sensor position relative to frame (right) as shown in FIG. 3 in which:

A—Angle at which sensor assembly points at eye relative to bottom of the frame
B—Angle at which the sensor assembly is adjusted for each user through changing the tilt on the frame
C—X Distance between centre of pupil and sensor assembly
D—Eye
E—Sensor unit
F—Distance from centre of frame to centre of sensor unit
G—Degree of wrap on frame to provide optimal vision for the user
H—Toe in of sensor unit to counteract the wrap on the frame The above metrics (see FIG. 3) are adjusted to a fixed secure position with the key adjustment metrics:

2. Frame
   Adjust tilt of arm by bending at hinge point (see FIG. 1, D)
   a. Adjustment of arms to provide stable latching mechanism to the users head and comfort (As per standard optometrist fitting procedures)

3. Nose Piece
   a. Adjustment of sensor assembly relative to eye up/down to obtain the correct angle at the eye (see FIG. 3, A)
   b. Adjustment of sensor assembly relative to eye towards and away (see FIG. 2, B)

4. Sensor Assembly
   a. 2 different angles are used to obtain the greatest coverage across the population. (see FIG. 3, A)

The frame provides a stable platform for maintaining a fixed static position for the sensor assembly in the correct location relative to the eye (see FIG. 1). The frame carries the following key features for good QOS from the largest portion of the population:

1. Tilt of frame (see FIGS. 2 and 3, B)
2. Intraocular spacing of sensor assembly (see FIG. 3, F)
3. Frame wrap (see FIG. 3, G)
4. Adjustable nose piece with fixed locators (see FIG. 2, A)

Figure 5:
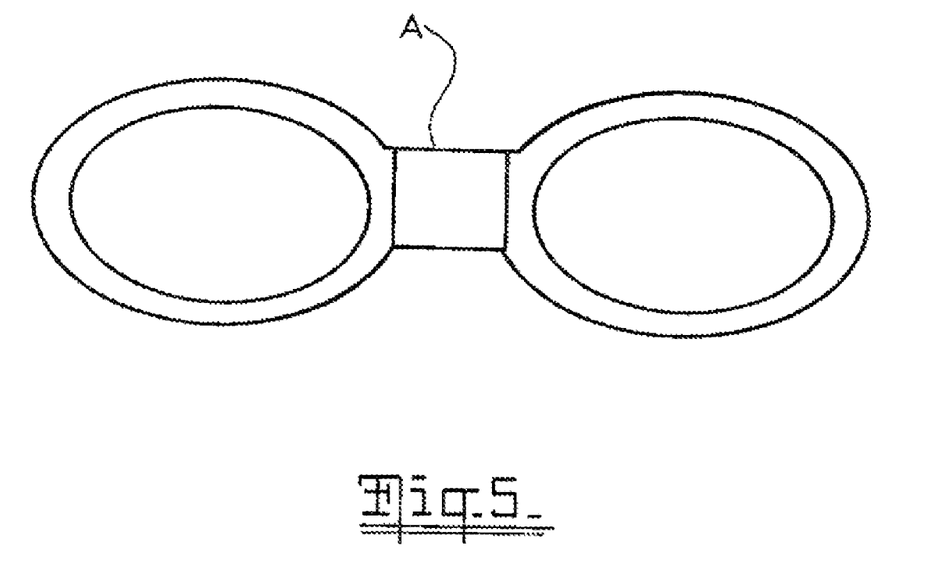
FIG. 5 shows the nose bridge relative to the ocular frames.

The nose piece sits in the centre of the frame (see FIG. 5 A) and provides one of the key fitment metrics. This is achieved through a fixed adjustable range provided by a series of holes on the adjustment plate with screws holding nose piece securely in position (see FIG. 1, B).

Figure 4:
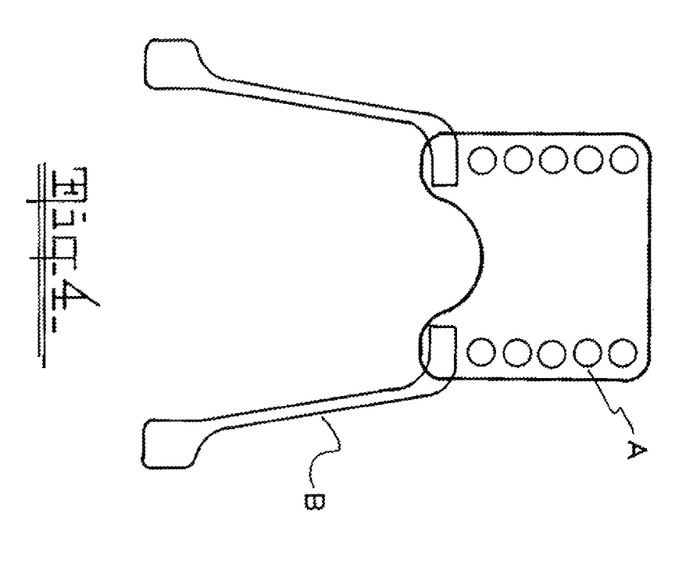
FIG. 4 illustrates one embodiment of the nose bridge of this invention.

As shown in FIG. 4 the holes A allow adjustable, fixed positions for the adjustable metal nose pad arms B Nose bridge location on frame is shown in FIG. 4 in which A is a slot for nose piece to provide adjustment in the Y axis.

The nose bridge provides key fitment metrics to obtain good QOS from a user:

1. Adjustment of sensor assembly relative to eye up/down by sliding the plate up and down (see FIG. 5, A)
2. Adjustment of sensor assembly relative to eye towards and away by bending nose pad arms (see FIG. 4, B).

Alternative systems for adjusting the nose piece are also within the scope of this invention.

Figure 6:
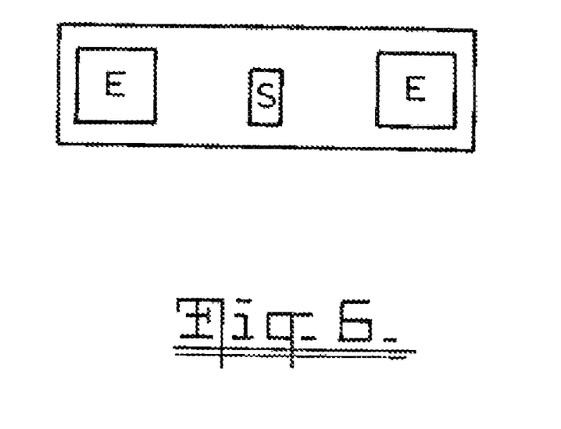
FIG. 6 schematically illustrates the arrangement of the sensor unit.

The sensor assembly is a plastic assembly which encapsulates the sensor S and emitters E in cavities within the frame with the following key features:
1. Creates an aperture for the sensor element S to collect targeted information from the correct region for good QOS
2. The emitters are arranged at 2 angles to cover largest portion of population
3. 3% carbon filled ABS plastic is used to absorb IR light and prevent leakage of IR light from the emitter cavities to sensor cavities.

The emitters provide pulses of invisible IR light (wavelength 940 nm) from an LED positioned about 13+/−3 mm below and 12+/−3 mm in front of the eye, housed in a frame that could also hold prescription lenses or sunglasses, if needed (FIG. 1). The IR pulses are brief (<100 microsec) and repeated at a frequency of 500 Hz. They are directed up in a 30 degree beam centered on the lower edge of the upper eyelid. The total IR light reflected back from the eye and eyelids is detected by the matched phototransistor beside the LED.

Figure 10:
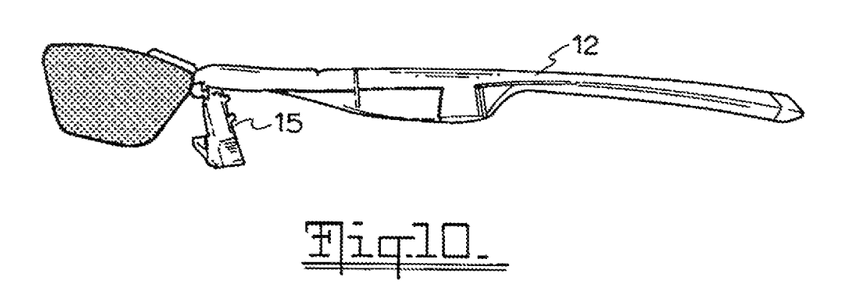
FIG. 10 illustrates the pivoting of the ocular lenses in the embodiment shown in FIG. 7.
Figure 11:
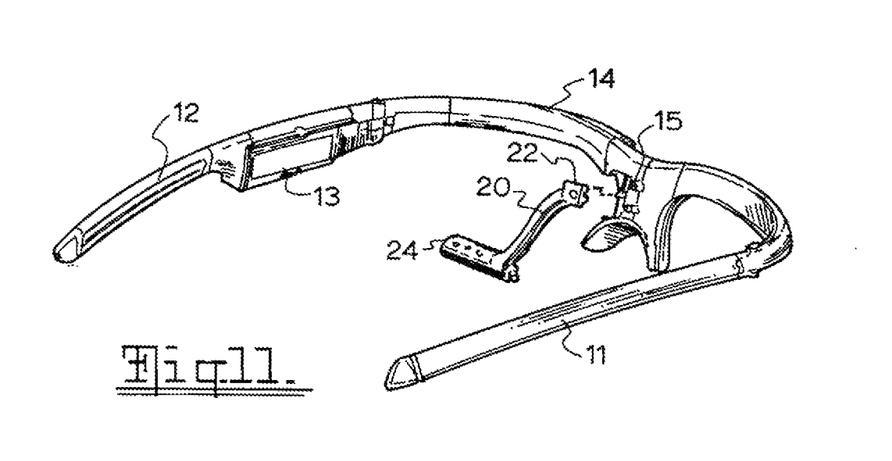
FIG. 11 is a rear view of the frame of FIG. 7 illustrating the attachment of the sensor arm.
Figure 12:
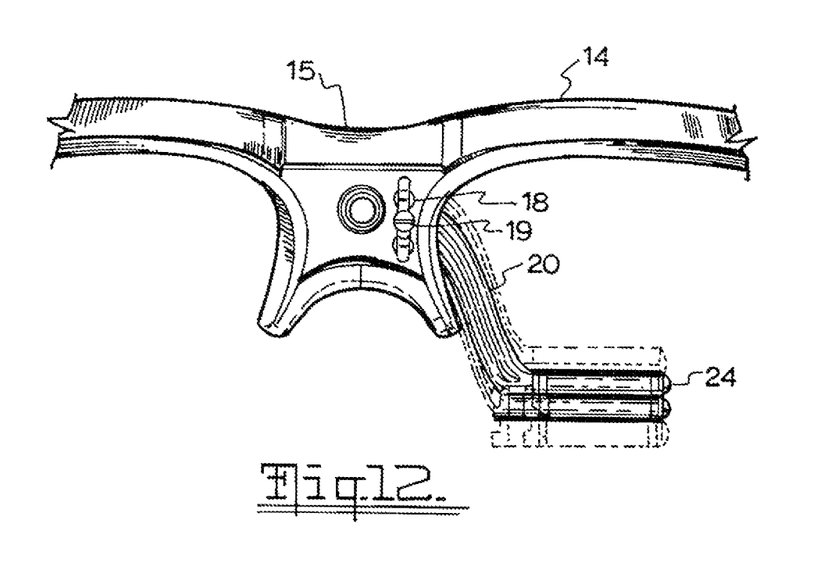
FIG. 12 is a detail illustrating the sensor arm adjustment mechanism.
Figure 13:
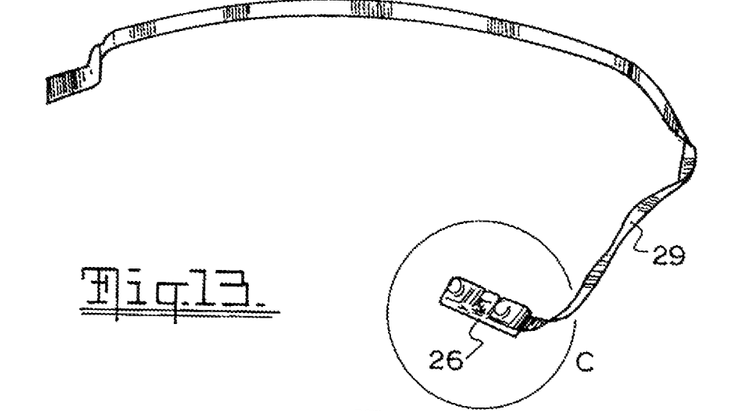
FIG. 13 illustrates the sensor pad unit with cable used in the embodiment of FIG. 7.

In the embodiment of the invention illustrated in FIGS. 7 to 16 the frame consists of ear stems 11 and 12. These may be of the wrap around type to maintain a stable position on the wearers head. An elastic strap may also be used to secure the frame to the head. The ear stem 12 incorporates an electronics module 13 which includes a microprocessor connected by a cable 29 to the sensor pad 26 shown in detail in FIG. 14. The ocular frame 14 incorporates a central nose bridge 15. The lenses are secured to lens attachment unit 16. The lenses may be of any type including prescribed lenses or sun protection lenses and may be clear or tinted as shown in FIGS. 9A and B. The unit 16 incorporates pivot pins 17 cooperating with pin recesses 17A that enable the lenses to be flipped up as shown in FIG. 10. The pins are shaped to provide two stable positions namely parallel to the face and at right angles to the face when flipped up. A nose adjustment piece 30 is attached to the unit 16. The attachment piece 30 comes in a range of incrementally changing sizes to suit a range of facial and nose types.

Figures 7, 9A:
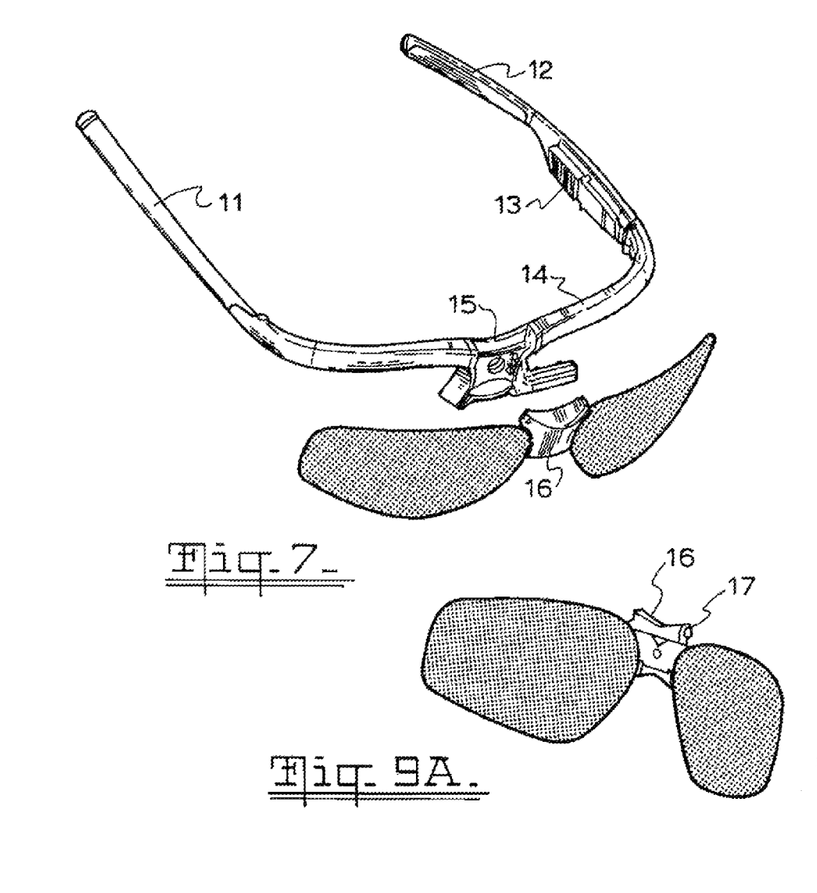
FIG. 7 is an exploded view of the frame of this invention in a second embodiment.
Figure 8:
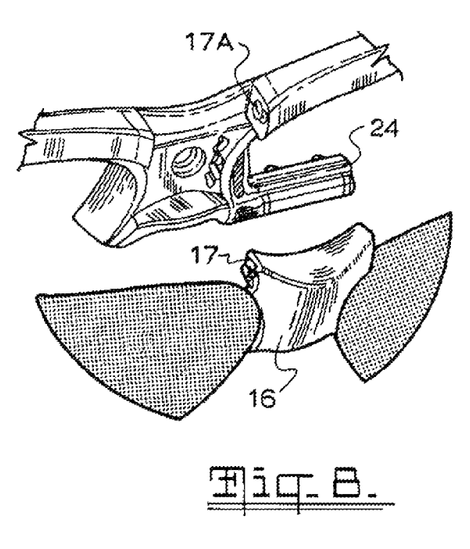
FIG. 8 is detailed view of FIG. 7.
Figure 9B:
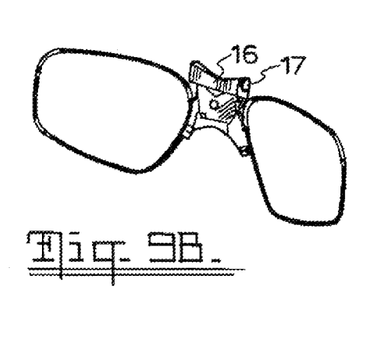
FIG. 9 illustrates the interchangeability of the ocular lenses.

The sensor arm 20 has attachment portion 22 at one end which is secured to the unit 16 by screw 19 and the sensor pod 24 at its other end. The slot 18 in unit 16 provides a number of vertical positions for the sensor arm attachment so that the position of the sensor pod 24 can be adjusted relative to the eye.

Figure 14:
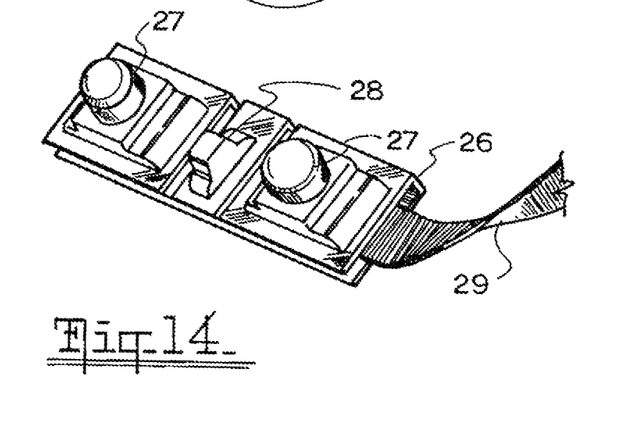
FIG. 14 is a detailed view of the sensor pad.
Figure 15:
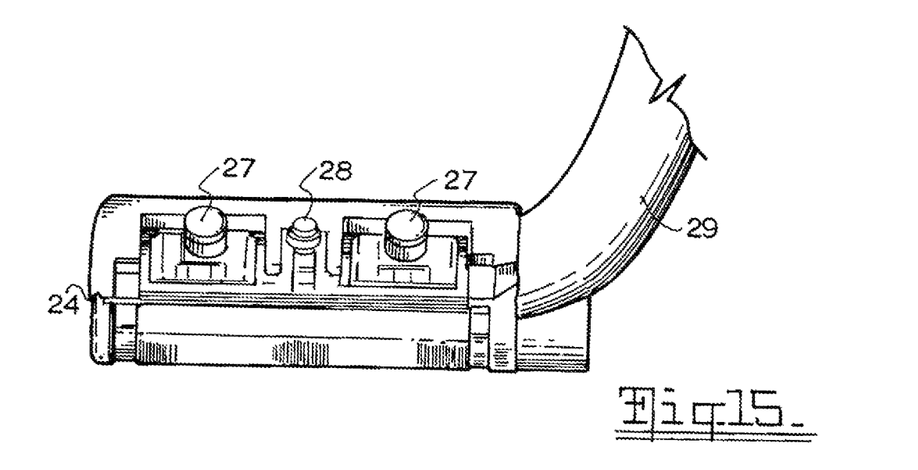
FIG. 15 is a view of the sensor pod incorporating the sensor pad of FIG. 14.

The sensor pad 26 is fitted to the pod 24 so that the sensors are resiliently mounted in the pod. The sensor pad consists of the emitters 27 and the receiver/detector 28. Each emitter 27 and detector 28 is individually mounted on a resilient finger.

The sensor pod 24 may be rotated through 10° of arc to further adjust the sensors relative to the eye. The sensor pod 24 or sensor arm 20 may be of variable length to suit a range of eye widths.

Figures 16, 17A, 17B:
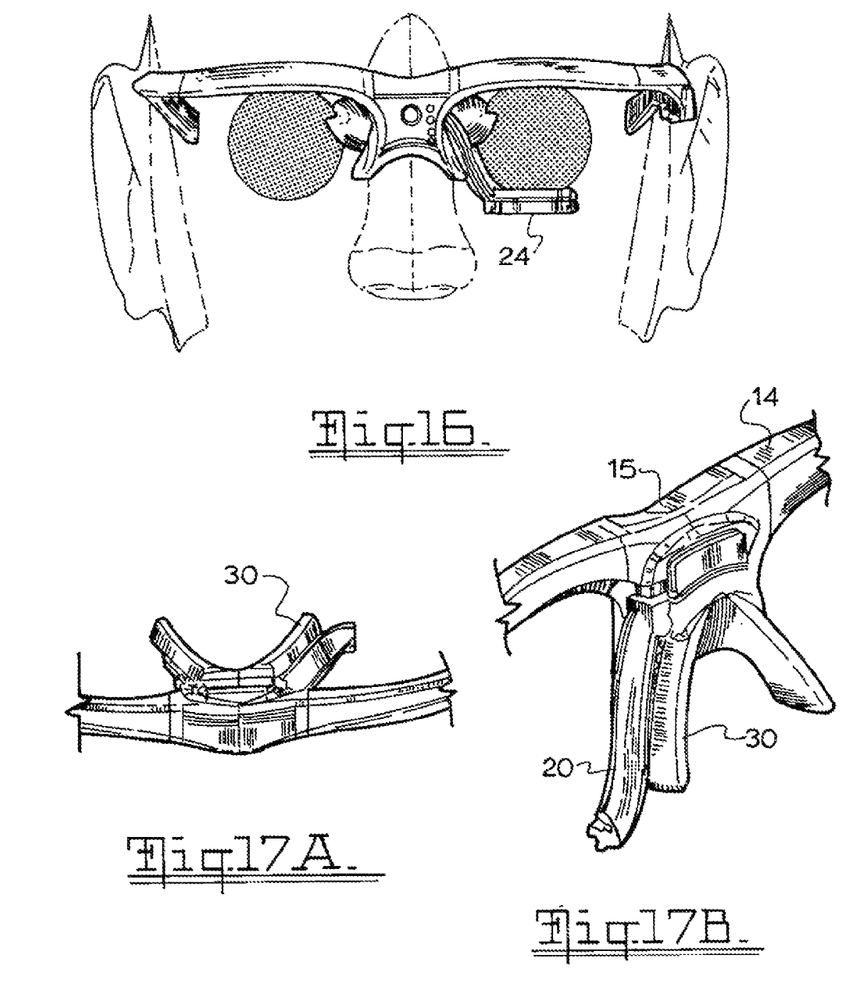
Figure 17C:
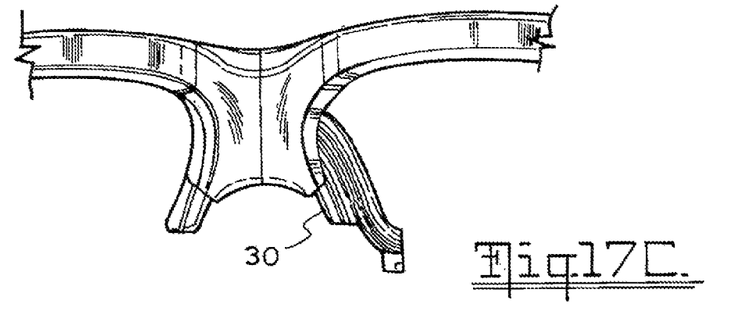
Figure 18A:
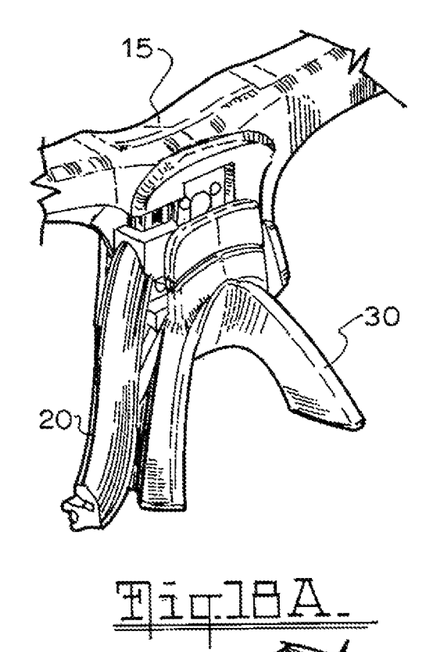
FIGS. 18A and B illustrates 2 views of the frame of this invention with a second nose adjustment piece.
Figure 18B:
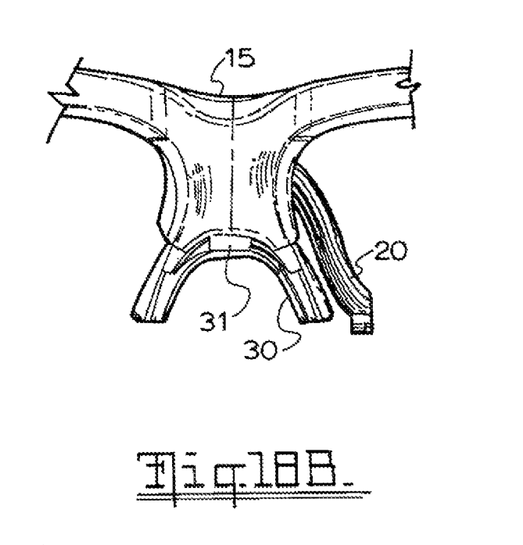
Figure 19A:
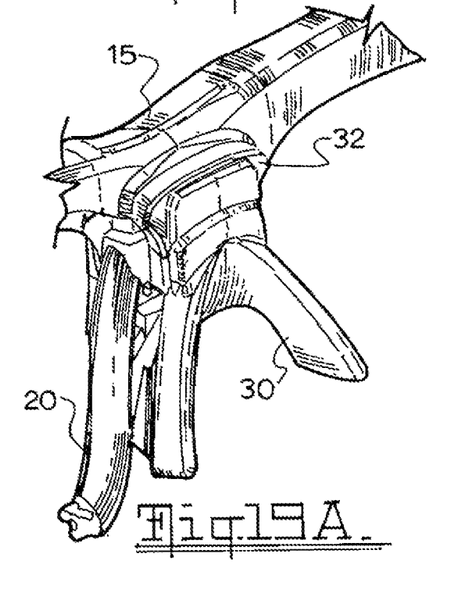
FIGS. 19A and B illustrates 2 views of the frame of this invention with a third nose adjustment piece.
Figure 19B:
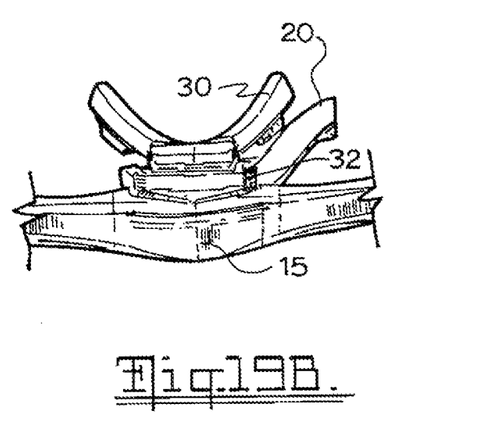

The position of the frame relative to the face is adjusted by selecting a nose piece 30 from a range of nose pieces. In FIGS. 17-19 three nose pieces 30 are shown which explain the incremental adjustments which can be made. FIG. 17 illustrates a base nose support 30 while FIG. 18 illustrates a nose support with an incremental vertical adjustment 31. FIG. 19 illustrates the nose piece with an incremental horizontal adjustment 32 to place the frame further away from the face.

By using combinations of one or more of the incremental vertical and horizontal adjustments a wide range of facial types can be accommodated.

In the embodiment shown in FIGS. 7 to 16 a microprocessor 13 housed in the arm 12 of the glasses controls the timing, duration and intensity of IR pulses, and digitizes the analogue output from the sensor (0 to 3.3 volts). The digital output from the glasses is sent via a light cable either to a bench-top processing unit for laboratory experiments, or to a unit installed in a vehicle for use while driving. The digitized output from the phototransistor represents the amount of IR light reflected back from the eye and eyelids. This is influenced by several factors, such as the shape and reflectance of the reflecting surface (highly pigmented skin reflects less than white skin). The surface of the cornea is approximately spherical and about 10 mm in diameter. As it rotates with eye movements, the angle of the reflecting surface of the eye changes in relation to the sensor. However, the major factor affecting the amount of reflected light that is measured is the distance between the reflecting surface and the sensor. This changes with corneal movement in any direction, and also with eyelid closure. It is this changing proximity of the reflecting surface in relation to the sensor that forms the basis of the system as described in WO 03/039358 for monitoring eye and eyelid movements. Differences in the reflectance of the cornea, iris, scleral conjunctiva, and the skin of the eyelids are also involved but they are probably less important than previously assumed. Software developed specifically for the system as described in WO 03/039358 uses period-amplitude analysis of both the position and velocity signals to derive a wide range of variables characterizing eye and eyelid movements.

In fitting the frames to each user a technician needs to be guided by the quality of the signal received from the detector to ensure that the fitting will ensure that analyzable signals are being received. The technician selects an appropriate nose piece 30 and the adjusts the sensor arm 20 until an optimum signal is received. Those skilled in the art will realize that this invention provides a practical and convenient spectacle frame for collecting eye movement data. Those skilled in the art will also realize that the spectacle frames may be arranged in other embodiments apart from those described without departing from the core teachings of this invention.

The invention claimed is:

1. A spectacle frame for use in an eye monitoring system which includes
    a) a nose bridge connecting a pair of ocular frames
    b) a sensor unit adjustably attached to said nose bridge said sensor unit incorporating a signal emitter and a signal detector recessed into the surface of the unit to reduce the proportion of signal received by said detector which is not from the signal emitter reflected by the eye or eyelids
    c) said nose bridge incorporating an adjustment mechanism for adjusting the vertical position of said sensor unit relative to the eye
    d) a frame arm extending from the outer edge of each ocular frame adapted to fit over the ear of a wearer wherein one of said frame arms incorporates a microprocessor for controlling the sensor unit.

2. A spectacle frame as claimed in claim 1 in which the adjustment mechanism includes a variably sized component that supports the nose bridge on the nose of the wearer.

3. A spectacle frame as claimed in claim 1 in which the sensor unit is mounted on the free end of an arm which is attachable at its other end to a range of locations on the nose bridge to fine tune the positioning of the sensor unit relative to the eye.

4. A spectacle frame as claimed in claim 1 in which the sensor unit is connected to the microprocessor by a cable located in the ocular frame and frame arm containing the microprocessor.

5. A spectacle frame as claimed in claim 1 in which the sensor unit includes at least one infra red emitter and one collector of reflected infra red light.

6. A spectacle frame as claimed in claim 5 in which there are two infra red emitters and one infra red sensor which are set into recesses in the ocular frame.

7. A spectacle frame as claimed in claim 6 in which the frame material around the sensor unit absorbs infra red wavelengths.

8. A spectacle frame for use in an eye monitoring system which includes
- a) a pair of ocular frames at least one of which has a sensor unit adapted to be positioned adjacent an eye of the wearer
- b) a nose bridge connecting said ocular frames and incorporating an adjustment mechanism for adjusting the vertical position of said sensor unit relative to the eye
- c) a frame arm extending from the outer edge of each ocular frame adapted to fit over the ear of a wearer said frame arm being pivotally connected to said ocular member by a hinge that is adjustable
- d) said sensor unit incorporating a light emitter and a light detector recessed into the surface of the unit to reduce the proportion of signal received by said detector which is not from the signal emitter reflected by the eye or eyelids.

9. A spectacle frame as claimed in claim 8 in which the sensor unit includes at least one infra red emitter and one collector of reflected infra red light.

10. A spectacle frame as claimed in claim 9 in which there are two infra red emitters and one infra red sensor which are set into recesses in the ocular frame.

11. A spectacle frame as claimed in claim 9 in which one frame arm incorporates an electronic device for controlling the infra red emitter and for receiving the signals received by the collector.

* * * * *